(12) United States Patent
Yang et al.

(10) Patent No.: US 11,733,258 B2
(45) Date of Patent: Aug. 22, 2023

(54) NUCLEIC ACID EXTRACTING DEVICE

(71) Applicant: Industrial Technology Research Institute, Hsinchu (TW)

(72) Inventors: Chih-Wen Yang, Taoyuan (TW); Ruey-Shyan Hong, Taoyuan (TW); Tzu-Hui Wu, Chiayi County (TW); Ting-Hsuan Chen, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 205 days.

(21) Appl. No.: 17/113,115

(22) Filed: Dec. 7, 2020

(65) Prior Publication Data

US 2021/0172972 A1 Jun. 10, 2021

Related U.S. Application Data

(60) Provisional application No. 62/945,897, filed on Dec. 10, 2019.

(30) Foreign Application Priority Data

Nov. 3, 2020 (TW) ................................. 109138168

(51) Int. Cl.
*G01N 35/10* (2006.01)
*C12N 15/10* (2006.01)
(Continued)

(52) U.S. Cl.
CPC ..... *G01N 35/1065* (2013.01); *B01F 27/0724* (2022.01); *B01F 27/11251* (2022.01);
(Continued)

(58) Field of Classification Search
None
See application file for complete search history.

(56) References Cited

U.S. PATENT DOCUMENTS 6,374,684 B1 4/2002 Dority
7,238,522 B2 7/2007 Hebel et al.
(Continued)

FOREIGN PATENT DOCUMENTS

CN 104059848 9/2014
CN 105441318 3/2016
(Continued)

OTHER PUBLICATIONS

"Search Report of Europe Counterpart Application", dated May 28, 2021, pp. 1-7.
(Continued)

*Primary Examiner* — P. Kathryn Wright
(74) *Attorney, Agent, or Firm* — JCIPRNET

(57) ABSTRACT

A nucleic acid extracting device includes a reagent containing unit, a mixing unit, and a flow channel unit. The reagent containing unit contains a specimen, a magnetic bead, and a reagent for extracting. The mixing unit includes a mixing chamber and a stirring assembly. The mixing chamber includes a chamber portion and a tube portion. The stirring assembly includes a main body and an extension. The main body is provided in the chamber portion. The tube portion connects the chamber portion. And the extension connects the main body and extends into the tube portion. The extension and an inner wall of the tube portion have first and second gaps therebetween respectively along first and second directions of the tube portion. The first gap is less than the second gap. The flow channel unit is connected between the reagent containing unit and the mixing unit.

19 Claims, 6 Drawing Sheets

(51) Int. Cl.
  *B01F 27/072* (2022.01)
  *B01F 27/90* (2022.01)
  *B01F 27/1125* (2022.01)
  *G01N 35/00* (2006.01)

(52) U.S. Cl.
  CPC .......... *B01F 27/90* (2022.01); *C12N 15/1003* (2013.01); *C12N 15/1013* (2013.01); *G01N 2035/00534* (2013.01); *G01N 2035/00564* (2013.01); *G01N 2035/1053* (2013.01)

(56) References Cited

U.S. PATENT DOCUMENTS

| | | | |
|---|---|---|---|
| 9,789,481 | B2 | 10/2017 | Petersen et al. |
| 2003/0162304 | A1 | 8/2003 | Dority et al. |
| 2006/0011539 | A1 | 1/2006 | Lee et al. |
| 2008/0014576 | A1* | 1/2008 | Jovanovich ........... B01L 3/5027 422/50 |
| 2010/0285578 | A1* | 11/2010 | Selden .............. B01L 3/502715 536/25.4 |
| 2013/0122576 | A1* | 5/2013 | Kwon ................... B01L 7/5255 435/287.2 |
| 2015/0240292 | A1 | 8/2015 | Hanamura |
| 2018/0164196 | A1 | 6/2018 | Chen et al. |
| 2020/0030806 | A1* | 1/2020 | Irmscher ................... F04B 7/04 |

FOREIGN PATENT DOCUMENTS

| | | |
|---|---|---|
| CN | 105734045 | 7/2016 |
| CN | 106947683 | 7/2017 |
| JP | 2004508542 | 3/2004 |
| JP | 2006508343 | 3/2006 |
| JP | 2008241250 | 10/2008 |
| JP | 2011128019 | 6/2011 |
| JP | 2015534808 | 12/2015 |
| JP | 2018502309 | 1/2018 |
| JP | 2019518470 | 7/2019 |
| JP | 2019176831 | 10/2019 |
| TW | I390041 | 3/2013 |
| TW | I565803 | 1/2017 |
| TW | I591182 | 7/2017 |
| TW | 201903147 | 1/2019 |
| WO | 2006032044 | 3/2006 |
| WO | 2006136999 | 12/2006 |
| WO | 2010091080 | 8/2010 |
| WO | 2014066704 | 5/2014 |
| WO | 2016195963 | 12/2016 |
| WO | WO-2022104272 A1 * | 5/2022 .......... B01J 19/0046 |

OTHER PUBLICATIONS

Liu et al., "Bubble-induced acoustic micromixing", Lab on a Chip, vol. 2, Jan. 2002, pp. 151-157.

"Office Action of Japan Counterpart Application", dated Nov. 30, 2021, p. 1-p. 3.

"Notice of Allowance of Taiwan Counterpart Application," dated Aug. 6, 2021, pp. 1-4.

"Office Action of China Counterpart Application", dated May 10, 2023, p. 1-p. 8.

* cited by examiner

NUCLEIC ACID EXTRACTING DEVICE

CROSS-REFERENCE TO RELATED APPLICATION

This application claims the priority benefit of U.S. provisional application Ser. No. 62/945,897, filed on Dec. 10, 2019, and Taiwan application serial no. 109138168, filed on Nov. 3, 2020. The entirety of each of the above-mentioned patent applications is hereby incorporated by reference herein and made a part of this specification.

BACKGROUND

Technical Field

The disclosure relates to an extracting device, particularly to a nucleic acid extracting device.

Description of Related Art

Nucleic acid analysis is a method indispensable nowadays for the research or detection of genetics, molecular biology, or animal and plant diseases. Therefore, technologies related to the separation and extraction of nucleic acid have developed rapidly in recent years. There is a method for nucleic acid extraction that mixes the specimen, magnetic beads, and various reagents for nucleic acid extraction in a mixing chamber according to an established process and sequence, so that the nucleic acid of the specimen is bound to the magnetic beads before being separated from the magnetic beads. Timeliness is decisive factor in nucleic acid analysis. For example, for emerging infectious diseases, the faster the nucleic acid analysis of bacteria or viruses is completed, the faster the corresponding vaccine can be developed. However, general mixing devices cannot mix magnetic beads with reagents with enough efficiency, thus considerably prolonging the time for extracting and analyzing nucleic acid.

SUMMARY

The nucleic acid extracting device of the present disclosure includes a reagent containing unit, a mixing unit, and a flow channel unit. The reagent containing unit is adapted to contain at least one specimen, at least one magnetic bead, and at least one reagent for extracting. The mixing unit includes a mixing chamber and a stirring assembly. The mixing chamber includes a chamber portion and a tube portion. The stirring assembly includes a main body and an extension. The main body is provided in the chamber. The tube portion connects to the chamber. And the extension connects to the main body and extends into the tube portion. The extension and an inner wall of the tube portion have a first gap therebetween in a first direction of the tube portion. The extension and the inner wall of the tube portion have a second gap therebetween in a second direction of the tube portion. And the first gap is smaller than the second gap. The flow channel unit is connected between the reagent containing unit and the mixing unit. The specimen, the magnetic beads, and the reagent for extracting are adapted to flow from the reagent containing unit through the flow channel unit to the mixing chamber to be stirred and mixed by the stirring assembly.

Based on the above, in addition to the existing chamber, the mixing chamber of the present disclosure further has a tube portion extending from the chamber portion, and the stirring assembly correspondingly has an extension that extends into the tube portion. In addition, there are the first gap and the second gap of different sizes between the extension of the stirring assembly and the inner wall of the tube portion. In other words, the sizes of the gaps between the extension and the inner wall of the tube portion are not made uniformly. The non-uniform gaps between the extension of the stirring assembly and the tube portion cause the liquid to produce uneven capillary force. When the pump sucks air from an upper end of the mixing chamber, the liquid flows up and down in the tube portion repeatedly, re-dissolving the magnetic beads that are attached to the tube wall.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF THE EMBODIMENTS

The present disclosure provides a nucleic acid extracting device, adapted to mix magnetic beads and reagents efficiently.

Figure 1:
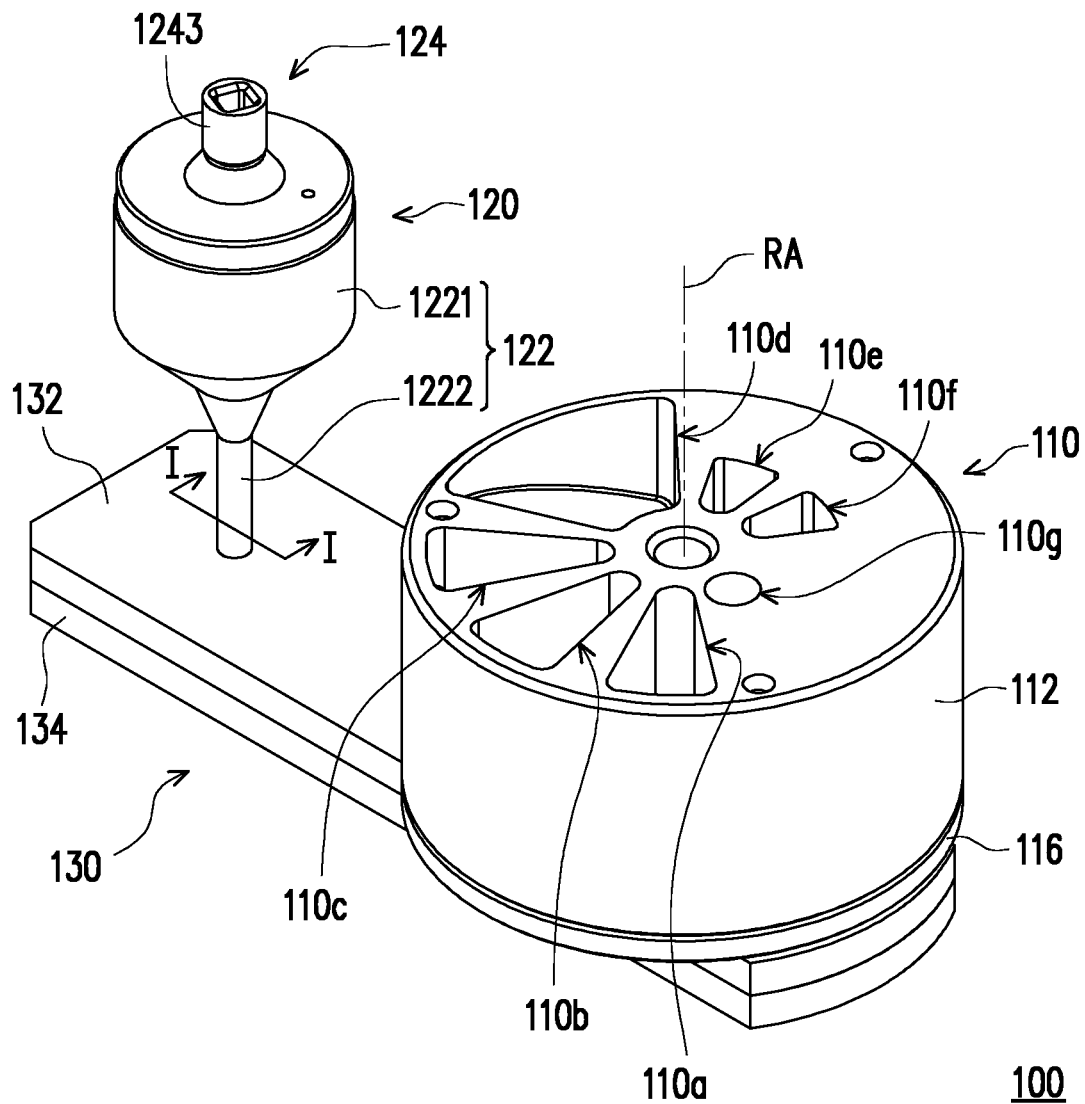
FIG. 1 is a stereogram of a nucleic acid extracting device according to an embodiment of the disclosure.
Figure 2:
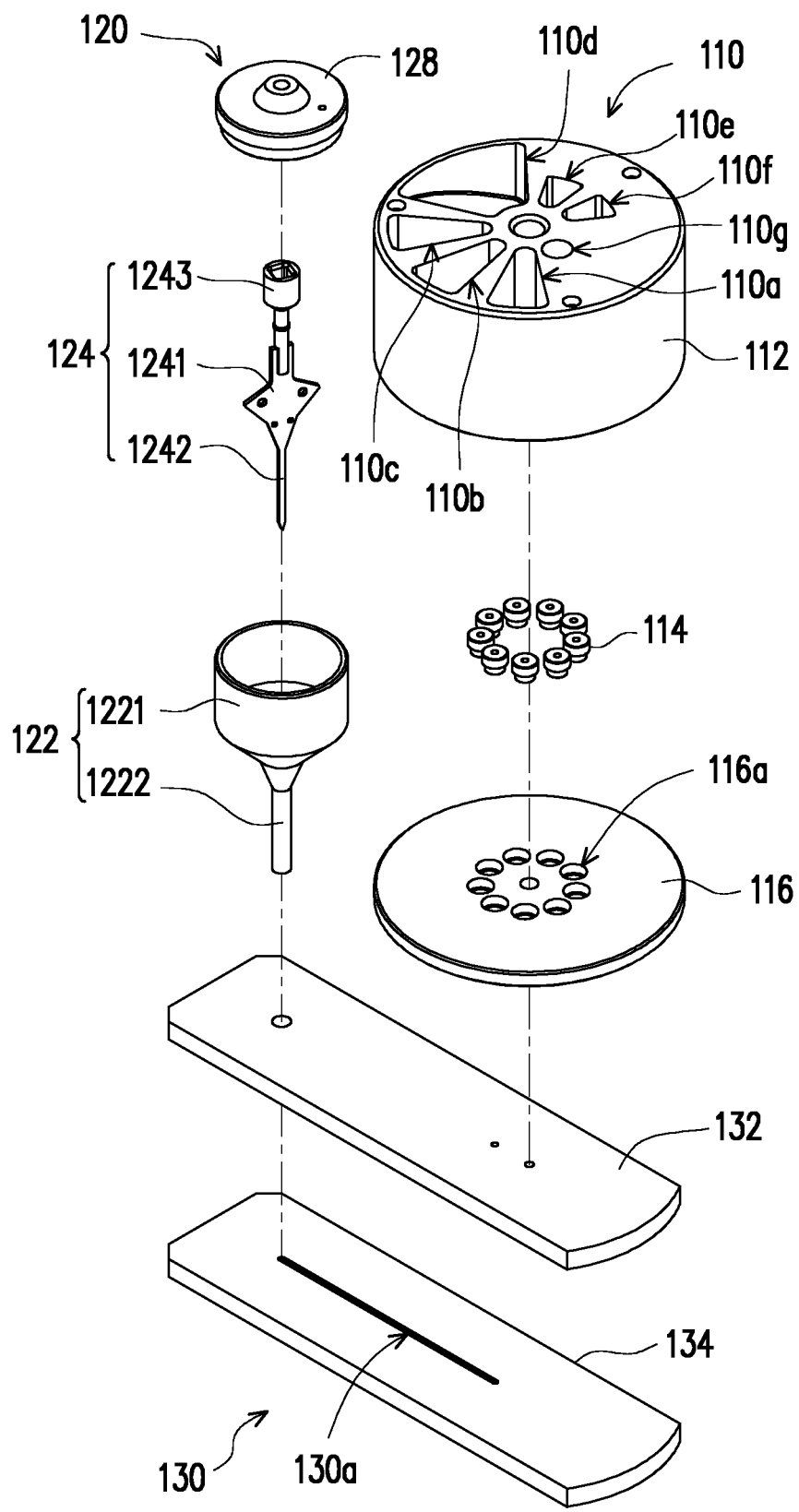
FIG. 2 is an exploded-view drawing of the nucleic acid extracting device of FIG. 1.
Figure 3:
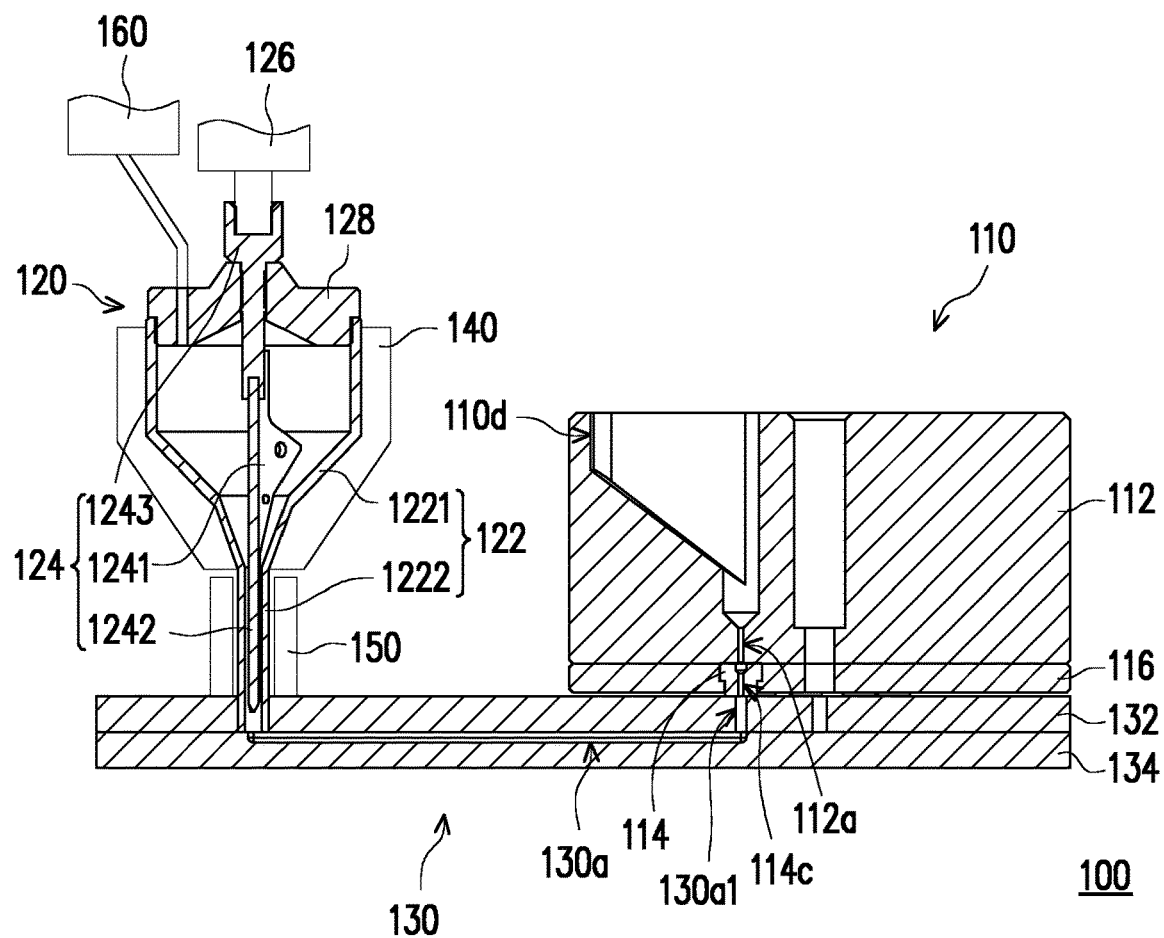
FIG. 3 is a cross-sectional view of the nucleic acid extracting device of FIG. 1.

FIG. 1 is a stereogram of a nucleic acid extracting device according to an embodiment of the disclosure. FIG. 2 is an exploded-view drawing of the nucleic acid extracting device of FIG. 1. FIG. 3 is a cross-sectional view of the nucleic acid extracting device of FIG. 1. In FIG. 1 to FIG. 3, a nucleic acid extracting device 100 of the present embodiment includes a reagent containing unit 110, a mixing unit 120, and a flow channel unit 130. The flow channel unit 130 includes, for example, an upper plate body 132 and a lower plate body 134 stacked together, and is connected between the reagent containing unit 110 and the mixing unit 120. The reagent containing unit 110 has a plurality of reagent chambers 110a to 110g, and the reagent chambers 110a to 110g are adapted to respectively contain a specimen, a plurality of magnetic beads, and various kinds of reagent for extracting. The mixing unit 120 includes a mixing chamber 122 and a stirring assembly 124. The specimen, the magnetic beads, and the reagent for extracting are adapted to flow from the reagent containing unit 110 through the flow channel unit 130 into the mixing chamber 122 according to an established process and sequence, and are stirred and mixed by the stirring assembly 124, so that nucleic acid of the specimen is bound to the magnetic beads before being separated from the magnetic beads.

In the present embodiment, the mixing chamber 122 includes a chamber portion 1221 and a tube portion 1222. The tube portion 1222 is connected between the flow channel unit 130 and the chamber portion 1221. An inner width of the tube portion 1222 is smaller than an inner width of the chamber portion 1221. Note that the cross sections of the tube portion 1222 and the chamber portion 1221 are circular in the present embodiment, so the aforementioned inner widths refer to inner diameters. The stirring assembly 124 includes a main body 1241 and an extension 1242. A width of the extension 1242 is smaller than a width of the main body 1241. The main body 1241 is provided in the chamber portion 1221, and the extension 1242 connects to the main body 1241 and extends into the tube portion 1222. When the stirring assembly 124 is driven to operate, the main body 1241 stirs the specimen, the magnetic beads, and/or the reagent for extracting in the chamber portion 1221, and the extension 1242 stirs the specimen, the magnetic beads, and/or the reagent for extracting in the tube portion 1222.

Figure 4:
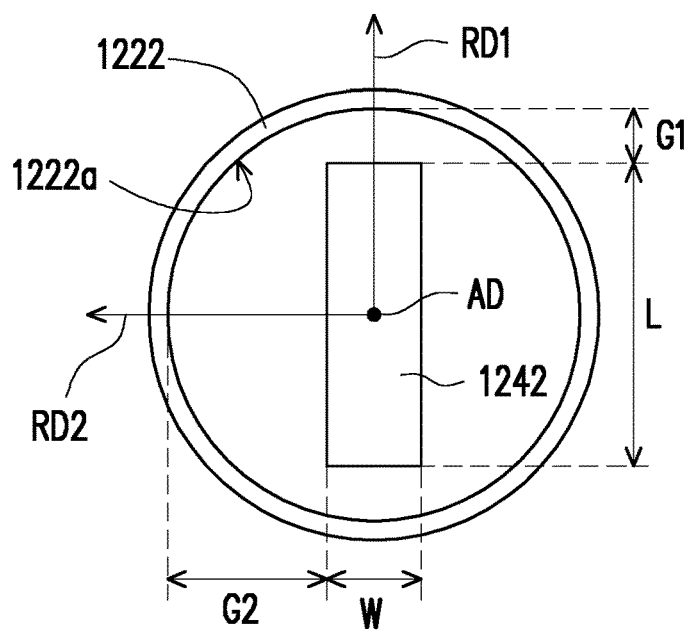
FIG. 4 is a cross-sectional view of the mixing unit of FIG. 1 along line I-I.

FIG. 4 is a cross-sectional view of the mixing unit of FIG. 1 along line I-I. Furthermore, in FIG. 4, the extension 1242 and an inner wall of the tube portion 1222 of the present embodiment have a first gap G1 therebetween in a first direction RD1 of the tube portion 1222 (that is, a radial direction perpendicular to an axial direction AD of the tube portion 1222). The extension 1242 and the inner wall of the tube portion 1222 have a second gap G2 therebetween in a second direction RD2 of the tube portion 1222 (that is, another radial direction perpendicular to the axial direction AD of the tube portion 1222). And, the first gap G1 is smaller than the second gap G2. In other words, sizes of the gaps between the extension 1242 and the inner wall of the tube portion 1222 are not uniform. As a result, the capillary force between the extension 1242 and the inner wall of the tube portion 1222 is uneven. Therefore, when the reagent flows in the mixing chamber 122 due to the drive of a pump 160 and/or the stir of the stirring assembly 124, the reagent at different places in the tube portion 1222 is stirred with different flow rates. Thus, bubbles are formed easily in the tube portion 1222, and the magnetic beads and the reagent are mixed speedily by the stir of the stirring assembly 124 and the disturbance of the bubbles.

Specifically, the tube portion 1222 of the present embodiment has a cylindrical pipe 1222a, and the extension 1242 is provided in the cylindrical pipe 1222a. The extension 1242 has a rectangular cross section, so that the extension 1242 has a first length L in the first direction RD1 and a second length W in the second direction RD2. And the first length L is greater than the second length W. This way, the sizes of the gaps between the extension 1242 and the inner wall of the tube portion 1222 may be made to be not uniform as described above. In other embodiments, the tube portion 1222 may have a pipe in other cross-sectional shapes, and the extension 1242 may have a cross section in other shapes, so that the gaps between the extension 1242 and the inner wall of the tube portion 1222 are not uniform. For example, the tube portion 1222 has a rectangular pipe, whereas the extension 1242 provided in the rectangular pipe has a circular cross section, a configuration that also includes non-uniform gaps. The present disclosure does not limit the practical shapes thereof.

In FIG. 3, the mixing unit 120 of the present embodiment includes an actuator 126 and a cover 128. The cover 128 covers the chamber portion 1221 of the mixing chamber 122. The stirring assembly 124 further includes a connection 1243. The connection 1243 may pass through the cover 128 and portionally protrude to the outside of the mixing chamber 122 and connects to the actuator 126. The actuator 126 is, for example, a motor, and is adapted to drive the stirring assembly 124 to rotate to perform the stir. In other embodiments, the actuator 126 may be other types of driving devices, and the present disclosure is not limited thereto. In addition, the mixing unit 120 may also not include the actuator 126, but there be an actuator included in other external devices to drive the stirring assembly 124 to operate.

As shown in FIG. 3, the nucleic acid extracting device 100 of the present embodiment further includes a heating device 140, a magnetic attracting device 150, and a pump 160. The heating device 140 is disposed beside the mixing chamber 122, and is adapted to heat the mixing chamber 122 to accelerate a reaction rate of the specimen and the reagent. The magnetic attracting device 150 is disposed movably outside the tube portion 1222, and is adapted to restrict the location of the magnetic beads by magnetic attraction, so as to prevent the magnetic beads from moving away from the tube portion 1222 unexpectedly due to the flow of the reagent. The pump 160 is connected to the mixing chamber 122 and is adapted to drive the specimen, the magnetic beads, and/or the reagent for extracting to move between the reagent containing unit 110 and the mixing chamber 122. The heating device 140 and the magnetic attracting device 150 may be disposed respectively at positions adjacent to the chamber portion 1221 and the tube portion 1222 as shown in FIG. 3, but the disclosure is not limited thereto. The nucleic acid extracting device 100 may also not include the heating device 140 and/or the magnetic attracting device 150, but there be a heating device and/or a magnetic attracting device included in other external devices to perform the heating and the magnetic attraction. When the heating and/or the magnetic attraction performed by the heating device 140 and/or the magnetic attracting device 150 is/are not required, the heating device 140 and/or the magnetic attracting device 150 may be driven to move away from the mixing chamber 122, or turn off the heating device 140 and/or the magnetic attracting device 150. In addition, the nucleic acid extracting device 100 may also not include the pump 160, but there be a pump included in other external devices to drive the specimen, the magnetic beads, and/or the reagent for extracting to flow.

In the present embodiment, the reagent for extracting may include a lysis buffer, a binding buffer, a washing buffer, and an elution buffer. As shown in FIG. 1, the reagent chamber 110a may be adapted to contain the specimen; the reagent chamber 110b may be adapted to contain the lysis solution; the reagent chamber 110c may be adapted to contain the binding buffer; the reagent chamber 110d may be adapted to contain the magnetic beads; the reagent chambers 110e and 110f may be adapted to contain the washing buffer; and, the reagent chamber 110g may be adapted to contain the elution buffer.

The specific operation flow of the nucleic acid extracting device 100 of the present embodiment is described below. First, the specimen in the reagent chamber 110a and the lysis buffer in the reagent chamber 110b flow from the reagent containing unit 110 through the flow channel unit 130 to the mixing chamber 122 by the drive of the pump 160. The heating device 140 heats the mixing chamber 122, and the stirring assembly 124 stirs the specimen and the lysis buffer in the mixing chamber 122, so that cell membranes of the specimen are destroyed by the lysis buffer to precipitate nucleic acid. Then, the binding buffer in the reagent chamber 110c and the magnetic beads in the reagent chamber 110d flow sequentially from the reagent containing unit 110 through the flow channel unit 130 to the mixing chamber 122 by the drive of the pump 160. The heating device 140 heats the mixing chamber 122, and the stirring assembly 124 stirs the specimen, the magnetic beads, and the binding buffer in the mixing chamber 122, so that the nucleic acid of the specimen is bound to the magnetic beads by the binding buffer. Then, the magnetic beads are prevented from moving by the magnetic attraction of the magnetic attracting device 150, and waste liquid generated by the reaction between the specimen and the reagent in the mixing chamber 122 is driven by the pump 160 to pass through the flow channel unit 130 to be discharged to the reagent containing unit 110; and the reagent containing unit 110 may include a waste liquid chamber or use an existing reagent chamber to contain the waste liquid.

Next, the washing buffer in the reagent chamber 110e flows from the reagent containing unit 110 through the flow channel unit 130 to the mixing chamber 122 by the drive of the pump 160. The stirring assembly 124 stirs the magnetic beads and the washing buffer in the mixing chamber 122 to wash the magnetic beads for the first time with the washing buffer. The magnetic attraction force of the magnetic attracting device 150 prevents the magnetic beads from moving, and the pump 160 drives the waste liquid generated in the mixing chamber 122 after the first wash to pass through the flow channel unit 130 to be discharged to the reagent containing unit 110; and the reagent containing unit 110 may include a waste liquid chamber or use an existing reagent chamber to contain the waste liquid. Then, the washing buffer in the reagent chamber 110f flows from the reagent containing unit 110 through the flow channel unit 130 to the mixing chamber 122 by the drive of the pump 160. The stirring assembly 124 stirs the magnetic beads and the washing buffer in the mixing chamber 122 to wash the magnetic beads for the second time with the washing buffer. The magnetic attraction force of the magnetic attracting device 150 prevents the magnetic beads from moving, and the pump 160 drives the waste liquid generated in the mixing chamber 122 after the second wash to pass through the flow channel unit 130 to be discharged to the reagent containing unit 110; and the reagent containing unit 110 may include a waste liquid chamber or use an existing reagent chamber to contain the waste liquid. The elution buffer in the reagent chamber 110g flows from the reagent containing unit 110 through the flow channel unit 130 to the mixing chamber 122 by the drive of the pump 160. The stirring assembly 124 stirs the magnetic beads and the elution buffer in the mixing chamber 122 to separate the nucleic acid from the magnetic beads with the elution buffer, and thereby extracting the nucleic acid.

In different steps of the foregoing operation flow, the amount of reagents in the mixing chamber 122 may be different. To make the mixing chamber 122 suitable for various amounts of reagents, a connecting end of the chamber portion 1221 to the tube portion 1222 may be designed to be funnel-shaped as shown in FIG. 1 to FIG. 3, such that inner widths of parts of the chamber portion 1221 gradually taper from top to bottom. This way, when the amount of the reagent in the mixing chamber 122 is large, the part with a larger inner width is capable of providing enough space to contain the reagent, and when the amount of the reagent in the mixing chamber 122 is small, the part with a smaller inner width is capable of preventing the reagent from being excessively dispersed in a horizontal direction due to the excessive width of the mixing chamber 122, so as to reduce the residual in corners of the chamber portion 1221. Correspondingly, the shape of the funnel-shaped part of the main body 1241 of the stirring assembly 124 provided in the chamber portion 1221 may also be changed accordingly. Specifically, the main body 1241 of the stirring assembly 124, which is disposed at the corresponding tapered part of the chamber portion 1221, may be designed as an airfoil and taper toward the extension 1242, so that even a small amount of reagent may be well stirred.

Figure 5:
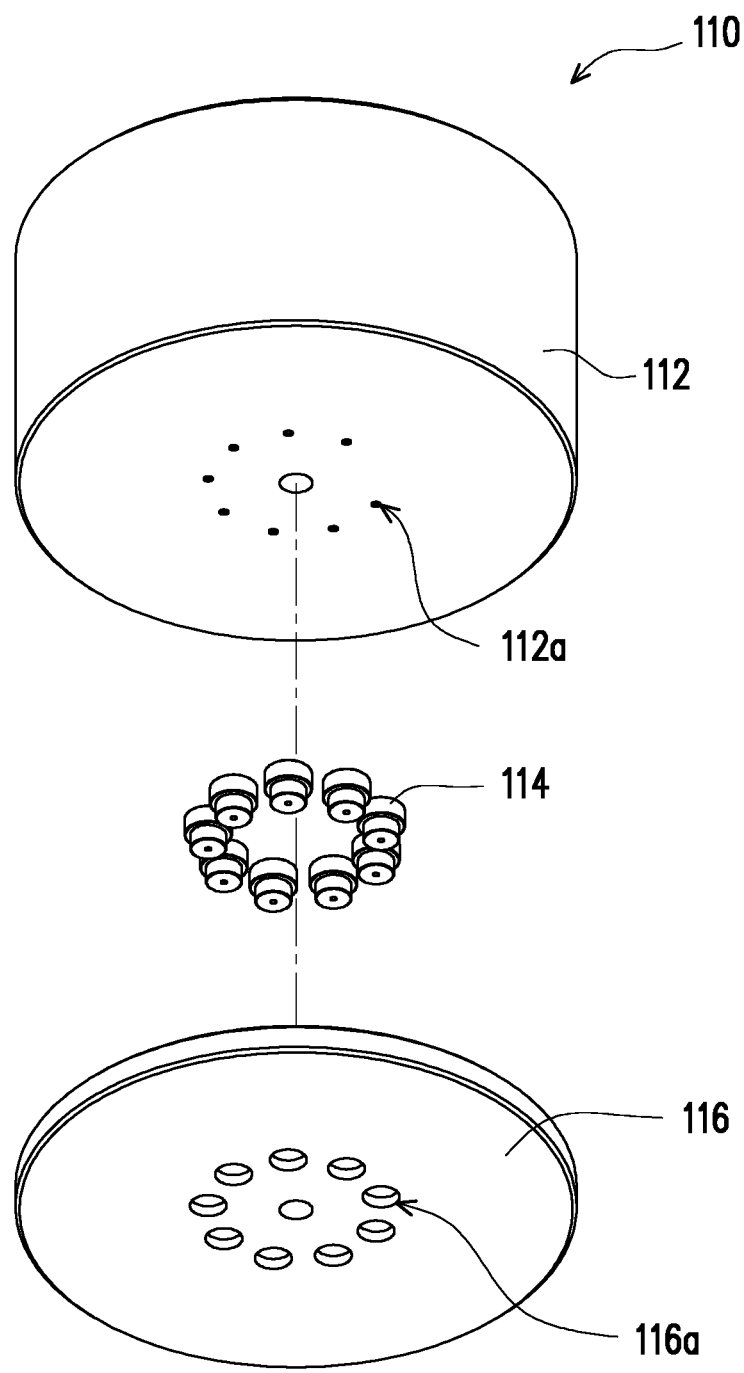
FIG. 5 is an exploded-view drawing of the reagent containing unit of FIG. 1.

FIG. 5 is an exploded-view drawing of the reagent containing unit of FIG. 1. In FIG. 3 and FIG. 5, the reagent containing unit 110 of the present embodiment includes a containing structure 112. The reagent chambers 110a to 110g are formed in the containing structure 112. A bottom of the containing structure 112 has a plurality of channels 112a, and the channels 112a are respectively connected to the reagent chambers 110a to 110g. And each of the reagent chambers 110a to 110g communicates with the flow channel unit 130 through the corresponding channel 112a.

Figure 6:
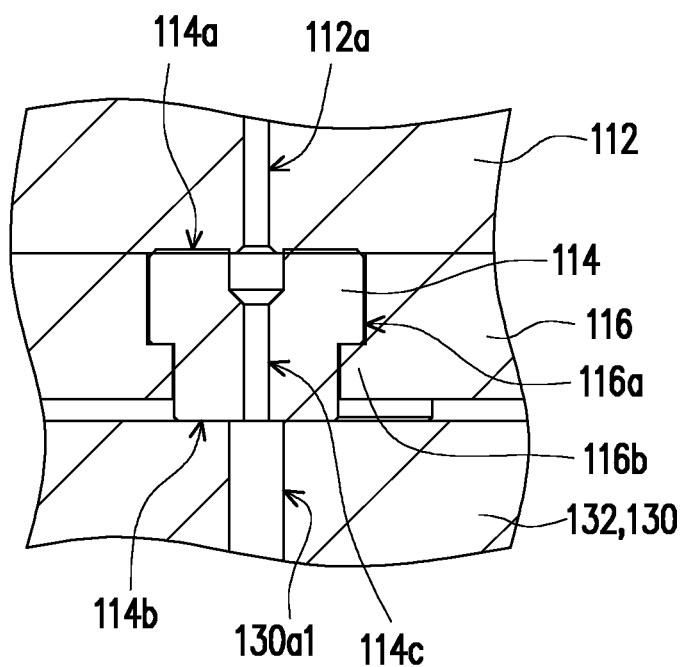
FIG. 6 is a locally enlarged view of the nucleic acid extracting device of FIG. 3.

Furthermore, the reagent containing unit 110 further includes a plurality of elastic seals 114 and a bottom plate 116. The elastic seals 114 are disposed at the bottom of the containing structure 112 and are corresponding respectively to the channels 112a. The bottom plate 116 is assembled to the bottom of the containing structure 112, for example, in a screw-locked manner, and each of the elastic seals 114 is restricted between the containing structure 112 and the flow channel unit 130. FIG. 6 is a locally enlarged view of the nucleic acid extracting device 100 of FIG. 3. In FIG. 6, each of the elastic seals 114 has a through hole 114c as well as a top surface 114a and a bottom surface 114b opposite to each other. The through hole 114c extends from the top surface 114a to the bottom surface 114b. Each of the elastic seals 114 is disposed in the bottom plate 116, and the top surface 114a and the bottom surface 114b of each elastic seal 114 respectively contact the containing structure 112 and the flow channel unit 130. The through hole 114c communicates with the corresponding channel 112a, so that each of the reagent chambers 110a to 110g may communicate with the flow channel unit 130 through the corresponding channel 112a and the corresponding through hole 114c. The material of each elastic seal 114 may be rubber or other elastic material suitable to perform sealing between the containing structure 112 and the flow channel unit 130, such that unexpected leakage of the reagent there may be prevented. In addition, each of the channels 112a of the containing structure 112 is, for example, a capillary, and the capillary resistance thereof further prevents the reagent from leaking.

Specifically, each of the elastic seals 114 is disposed in the opening 116a of the bottom plate 116. And each of the elastic seals 114 is in a stepped shape as shown in FIG. 6, and may be restricted by a flange 116b in the opening 116a to be at the bottom of the containment structure 112. The through hole 114c of each elastic seal 114 is adapted to communicate with an end 130a1 (marked in FIG. 6) of the flow channel 130a (marked in FIG. 2 and FIG. 3) provided between the upper plate body 132 and the lower plate body 134 of the flow channel unit 130.

In the present embodiment, the flow channel unit 130 has, for example, only one flow channel 130a, and one end of the flow channel 130a is connected to the mixing chamber 122. The reagent containing unit 110 is rotatably disposed on the flow channel unit 130 along a rotation axis RA (shown in FIG. 1) and is adapted to rotate, so that any one of the reagent chambers 110a to 110g may be correspond to the other end of the flow channel 130a (i.e., the end 130a1 shown in FIG. 6), such that one of the reagent chambers 110a to 110g communicates with the mixing chamber 122. In the present embodiment, the reagent containing unit 110 rotates via the drive of, for example, a motor or other suitable drivers. In other embodiments, the communication between the reagent chambers 110a to 110g and the mixing chamber 122 may also be switched by adopting other suitable methods and/or structures, and the present disclosure is not limited thereto.

Figure 7:
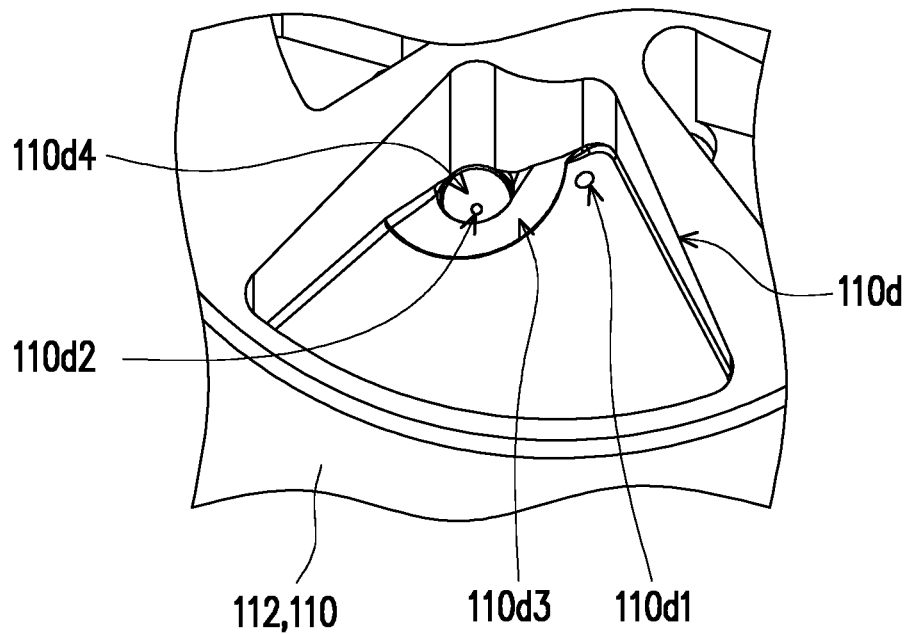
FIG. 7 is a locally enlarged view of the containing structure of FIG. 1.

FIG. 7 is a locally enlarged view of the containing structure of FIG. 1. In FIG. 7, in the present embodiment, the reagent chamber 110d corresponding to the magnetic beads has an inlet 110d1, an outlet 110d2, and a guide surface 110d3, and a bottom of the reagent chamber 110d has a recess 110d4. The outlet 110d2 is provided in the recess 110d4, and the recess 110d4 is adapted to contain the magnetic beads. The location of the inlet 110d1 is higher than the location of the outlet 110d2, and the guide surface 110d3 extends obliquely from the inlet 110d1 to the outlet 110d2. When the magnetic beads are to be moved to the mixing chamber 122 shown in FIG. 1, a suitable reagent may be driven to enter the reagent chamber 110d from the inlet 110d1, so that the reagent drives the magnetic beads to move out of the reagent chamber 110d from the outlet 110d2 and move to the mixing chamber 122 through the flow channel unit 130. Since the magnetic beads are collected to the lower recess 110d4 in advance, and the reagent flows downward from the inlet 110d1 which is above the location of the outlet 110d2, and drives the magnetic beads to move away from the reagent chamber 110d through the outlet 110d2, the magnetic beads are prevented from dashing out of the reagent chamber 110d due to the impact of the reagent.

Figure 8:
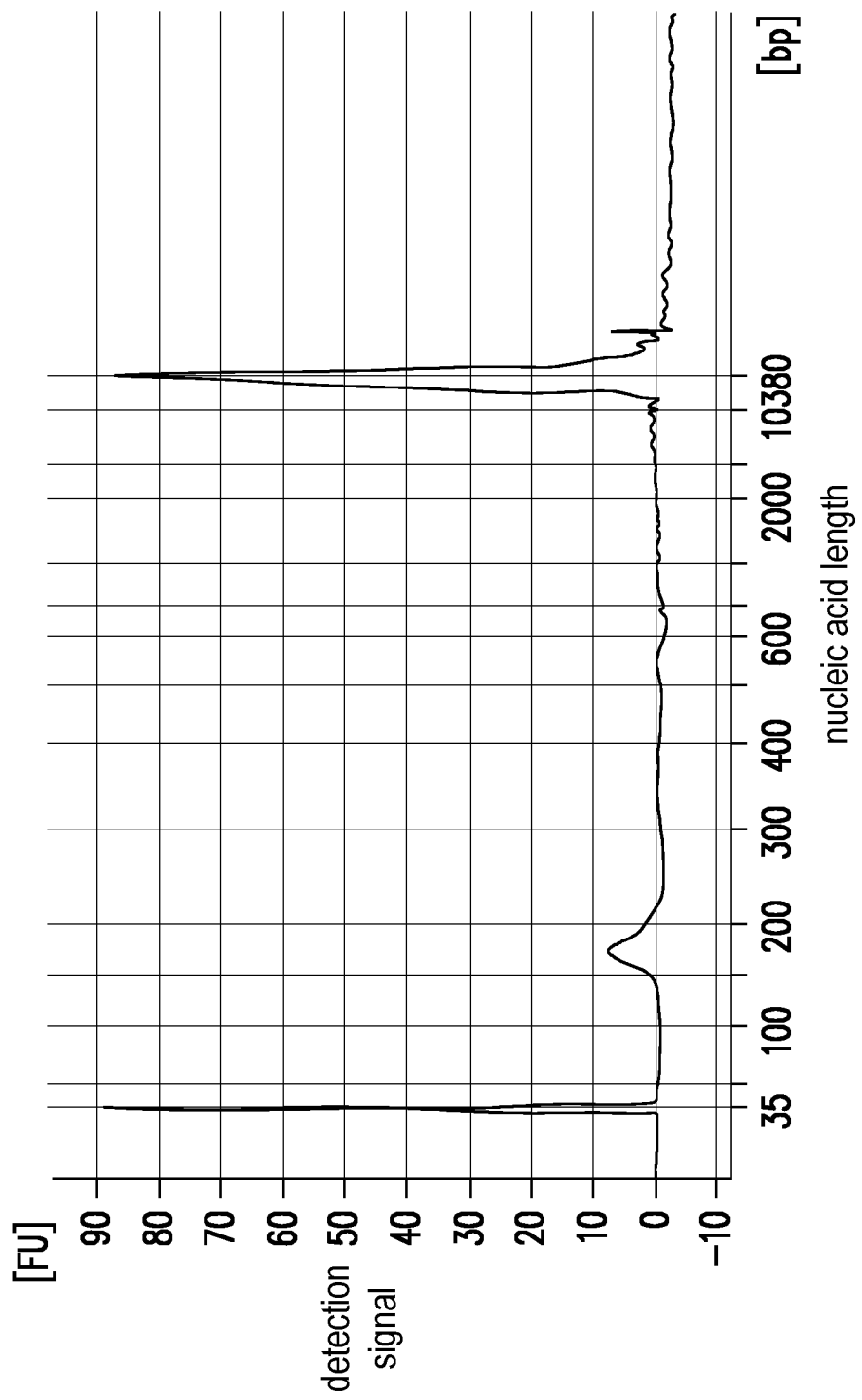
FIG. 8 shows a corresponding detection signal of the nucleic acid extracted by the nucleic acid extracting device of FIG. 1.

FIG. 8 shows a corresponding detection signal of the nucleic acid extracted by the nucleic acid extracting device of FIG. 1. As shown in FIG. 8, a significant detection signal appears between the nucleic acid length of 150 bp to 200 bp, indicating that the nucleic acid extracting device 100 of the present embodiment indeed extracts nucleic acid from the specimen.

In sum, in addition to the existing chamber, the mixing chamber of the present disclosure further includes a tube portion extending from the chamber portion, and the stirring assembly correspondingly includes an extension that extends into the tube portion. In addition, there are the first gap and the second gap of different sizes between the extension of the stirring assembly and the inner wall of the tube portion. In other words, the sizes of the gaps between the extension and the inner wall of the tube portion are not made uniformly. The non-uniform gaps between the extension of the stirring assembly and the tube portion cause the liquid to produce uneven capillary force. When the pump sucks air from the upper end of the mixing chamber, the liquid flows up and down in the tube portion repeatedly, re-dissolving the magnetic beads that are attached to the tube wall.

It will be apparent to those skilled in the art that various modifications and variations can be made to the structure of the disclosed embodiments without departing from the scope or spirit of the disclosure. In view of the foregoing, it is intended that the disclosure cover modifications and variations of the present disclosure provided they fall within the scope of the following claims and their equivalents.

What is claimed is:

1. A nucleic acid extracting device, comprising:
a reagent containing unit, configured to contain at least one specimen, at least one magnetic bead, and at least one reagent for extracting;
a mixing unit, comprising
a mixing chamber comprising a chamber portion and a tube portion; and
a stirring assembly, comprising a main body and an extension, the main body is provided in the chamber portion, the tube portion connects to the chamber portion, the extension connects to the main body and extends into the tube portion, the extension and an inner wall of the tube portion comprises a first gap therebetween in a first direction of the tube portion, the extension and the inner wall of the tube portion comprises a second gap therebetween in a second direction of the tube portion, the first gap and the second gap are located on the same plane which is perpendicular to an axial direction of the tube portion, the first gap is smaller than the second gap, and an inner width of the tube portion is smaller than an inner width of the chamber portion; and
a flow channel unit, connected between the reagent containing unit and the mixing unit, wherein the at least one specimen, the at least one magnetic bead, and the at least one reagent for extracting are configured to flow from the reagent containing unit through the flow channel unit to the mixing chamber to be stirred and mixed by the stirring assembly.

2. The nucleic acid extracting device according to claim 1, wherein an inner width of at least part of the chamber portion tapers from top to bottom, and the main body disposed in a corresponding tapered part of the chamber portion tapers toward the extension.

3. The nucleic acid extracting device according to claim 1, wherein a width of the extension is smaller than a width of the main body.

4. The nucleic acid extracting device according to claim 1, wherein the tube portion is connected between the flow channel unit and the chamber portion.

5. The nucleic acid extracting device according to claim 1, wherein the extension comprises a first length in the first direction and a second length in the second direction, and the first length is greater than the second length.

6. The nucleic acid extracting device according to claim 1, wherein the tube portion comprises a cylindrical pipe, and the extension is provided in the cylindrical pipe and comprises a rectangular cross section.

7. The nucleic acid extracting device according to claim 1, wherein the mixing unit comprises an actuator, and the actuator is connected to the stirring assembly and is adapted to drive the stirring assembly to rotate.

8. The nucleic acid extracting device according to claim 1, further comprising a heating device, wherein the heating device is disposed beside the mixing chamber and is adapted to heat the mixing chamber.

9. The nucleic acid extracting device according to claim 1, further comprising a magnetic attracting device, wherein the magnetic attracting device is disposed movably outside the tube portion and is adapted to prevent the at least one magnetic bead from moving away from the tube portion by magnetic attraction.

10. The nucleic acid extracting device according to claim 1, further comprising a pump, wherein the pump is connected to the mixing chamber and is adapted to drive the at least one specimen, the at least one magnetic bead, and the at least one reagent for extracting to move between the reagent containing unit and the mixing chamber.

11. The nucleic acid extracting device according to claim 1, wherein the reagent containing unit comprises a plurality of reagent chambers, and the plurality of reagent chambers are adapted to contain respectively the at least one specimen, the at least one magnetic bead, and the at least one reagent for extracting.

12. The nucleic acid extracting device according to claim 11, wherein the at least one reagent for extracting comprises a lysis solution, a binding buffer, a washing buffer, and an elution buffer, and part of the plurality of reagent chambers are adapted to contain respectively the lysis solution, the binding buffer, the washing buffer, and the elution buffer.

13. The nucleic acid extracting device according to claim 11, wherein one of the plurality of reagent chambers corresponding to contain the at least one magnetic bead comprises an inlet and an outlet, and a location of the inlet is higher than a location of the outlet.

14. The nucleic acid extracting device according to claim 13, wherein the reagent chamber corresponding to contain the at least one magnetic bead comprises a guide surface, and the guide surface extends obliquely from the inlet to the outlet.

15. The nucleic acid extracting device according to claim 13, wherein a bottom of the reagent chamber corresponding to contain the at least one magnetic bead comprises a recess, the outlet is provided in the recess, and the recess is adapted to contain the at least one magnetic bead.

16. The nucleic acid extracting device according to claim 11, wherein the reagent containing unit comprises a containing structure, the plurality of reagent chambers are formed in the containing structure, a bottom of the containing structure comprises a plurality of channels, the plurality of channels are connected respectively to the plurality of reagent chambers, and each of the plurality of reagent chambers communicates with the flow channel unit via a corresponding channel of the plurality of channels.

17. The nucleic acid extracting device according to claim 16, wherein each of the plurality of channels is a capillary.

18. The nucleic acid extracting device according to claim 16, wherein the reagent containing unit further comprises a plurality of elastic seals and a bottom plate, the plurality of elastic seals are disposed at the bottom of the containing structure and are corresponding to the plurality of channels respectively, the bottom plate is assembled at the bottom of the containing structure and each of the plurality of elastic seals is restricted between the containing structure and the flow channel unit, each of the plurality of elastic seals comprises a through hole as well as a top surface and a bottom surface opposite to each other, the through hole extends from the top surface to the bottom surface, each of the plurality of elastic seals is disposed in the bottom plate, the top surface and bottom surface respectively contact the containing structure and the flow channel unit, and the through hole connects to the corresponding channel of the plurality of channels.

19. The nucleic acid extracting device according to claim 11, wherein the flow channel unit comprises a flow channel, an end of the flow channel is connected to the mixing chamber, and the reagent containing unit is disposed rotatably on the flow channel unit and is adapted to rotate, so that any one of the plurality of reagent chambers corresponds to the other end of the flow channel.

* * * * *